US00PP24471P3

(12) United States Plant Patent
Schäfer

(10) Patent No.: US PP24,471 P3
(45) Date of Patent: May 20, 2014

(54) VARIETY OF BASIL PLANT NAMED 'GREEN FORTUNE'

(50) Latin Name: *Ocimum basilicum*
Varietal Denomination: Green Fortune

(75) Inventor: Udo Schäfer, Wolsier (DE)

(73) Assignee: Herbalea GmbH, Grolsheim (DE)

( * ) Notice: Subject to any disclaimer, the term of this patent is extended or adjusted under 35 U.S.C. 154(b) by 94 days.

(21) Appl. No.: 13/385,811

(22) Filed: Mar. 7, 2012

(65) Prior Publication Data

US 2013/0239275 P1 Sep. 12, 2013

(51) Int. Cl.
*A01H 5/00* (2006.01)

(52) U.S. Cl.
USPC ..... Plt./258

(58) Field of Classification Search
USPC ..... Plt./258
See application file for complete search history.

(56) References Cited

U.S. PATENT DOCUMENTS

PP13,486 P2 * 1/2003 Bowden et al. ..... Plt./258
PP16,260 P2 * 2/2006 Bennerup ..... Plt./258

OTHER PUBLICATIONS

UPOV PLUTO QZ Reference for 'Green Fortune' Feb. 15, 2011.*
Caes, Rudy and Wendy Haas. E-mail from Aug. 27, 2013 "Re: Denied Variety Name" regarding denomination of 'Dark Lady'.*

* cited by examiner

*Primary Examiner* — Wendy C Haas
(74) *Attorney, Agent, or Firm* — The Webb Law Firm

(57) ABSTRACT

'Green Fortune' is a new variety of basil plant having a tall and well-branched growth habit, violet flowers, a very spicy flavor and tolerance to low temperatures.

9 Drawing Sheets

Botanical classification: *Ocimum basilicum.*
Varietal denomination: 'GREEN FORTUNE'.

BACKGROUND OF THE NEW PLANT

The present invention comprises a new and distinct cultivar of basil plant, botanically known as *Ocimum basilicum* and hereinafter referred to by the cultivar name 'Green Fortune'.

The new variety was discovered and selected by the breeder in a cultivated environment in July of 2009 in Wolsier, Germany (located in the region of Brandenburg) as a naturally occurring open-pollinated new variety in a population of unpatented and unnamed *Ocimum basilicum* plants. Subsequently, the new variety was asexually reproduced by cuttings in Wolsier, Germany in 2010. Further asexual reproductions at the same location has demonstrated that the combination of characteristics as herein disclosed for the new cultivar are retained and reproduced true to type through successive generations of asexual reproduction.

The following observations, measurements and comparisons describe 8-week-old plants grown in an open field with full sun, watered as needed, and receiving weekly fertilization treatments accented with nitrogen in Wolsier, Germany. The plants were exposed to daytime temperatures of 20-30° C., and evening temperatures of 10-20° C. Color observations were taken under natural light, and the color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Green Fortune' which, in combination, distinguish this basil plant as a new and distinct cultivar:

1. Tall, well-branched, and rounded plant habit;
2. Fruity fragrance;
3. Aromatic taste;
4. Tolerant to *Fusarium oxysporum, Botrytis cinerea*, and *Pythium* sp.; and
5. Low temperature tolerance.

Further, the new variety exhibits an aromatic taste like basil variety 'Green Ball' (U.S. Plant Patent Application Publication Number 20130239274). However, 'Green Fortune' has a tall growth habit, while 'Green Ball' has a compact growth habit. The following Table 1 provides a further comparative listing of botanical characteristics of 'Green Fortune' and 'Green Ball'.

TABLE 1

| Botanical characteristics | 'Green Fortune' | 'Green Ball' |
|---|---|---|
| Height from soil to top of plant: | 55 cm. | 20 cm. |
| Leaf length: | 4 cm. | 2 cm. |
| Number of leaves per plant: | About 300 | Over 700 |
| Flower production: | Yes | No |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
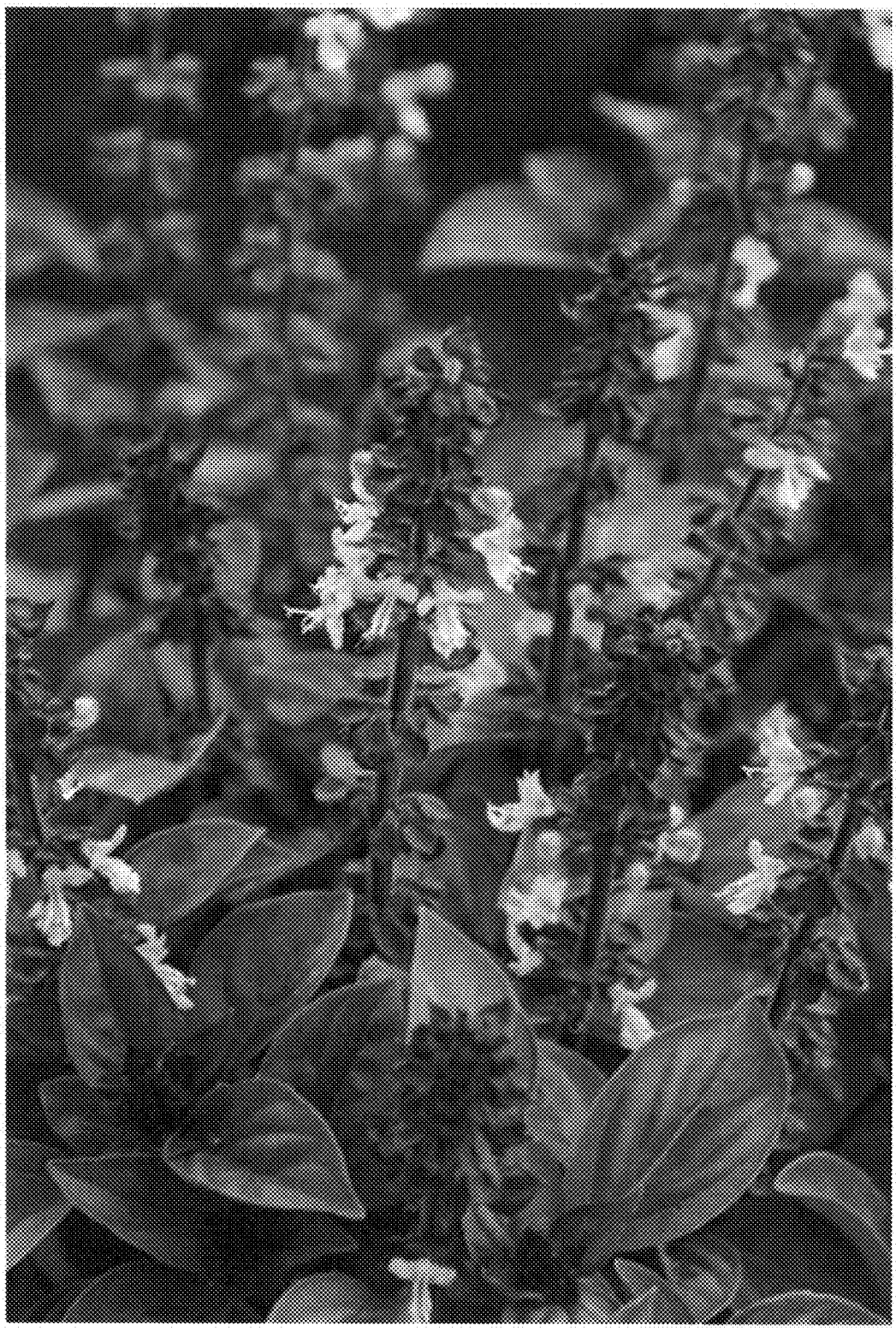
FIG. 1 is a photograph of the leaves and flowers of the new variety.
Figure 2:
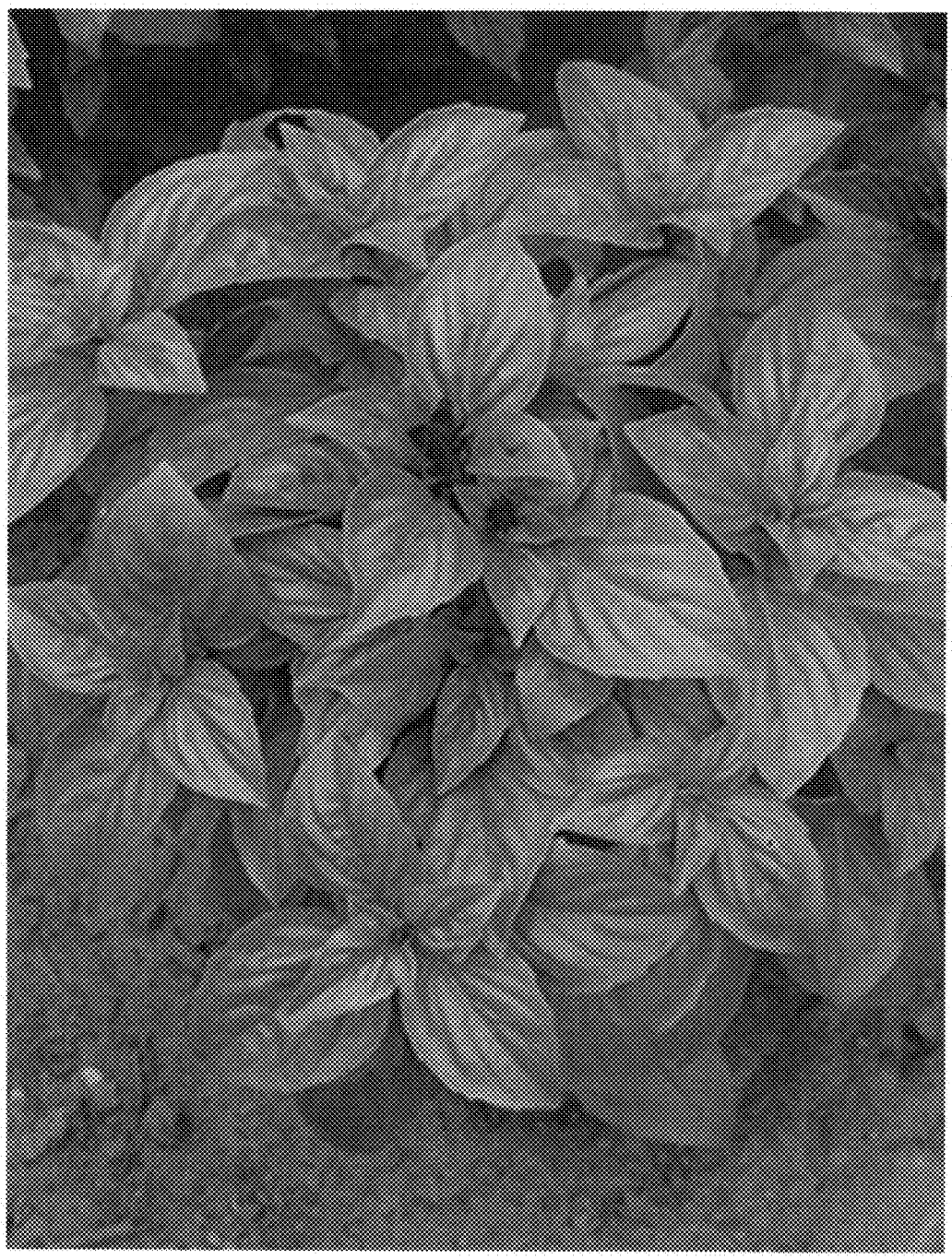
FIG. 2 is a photograph of the leaves of the new variety.
Figure 3:
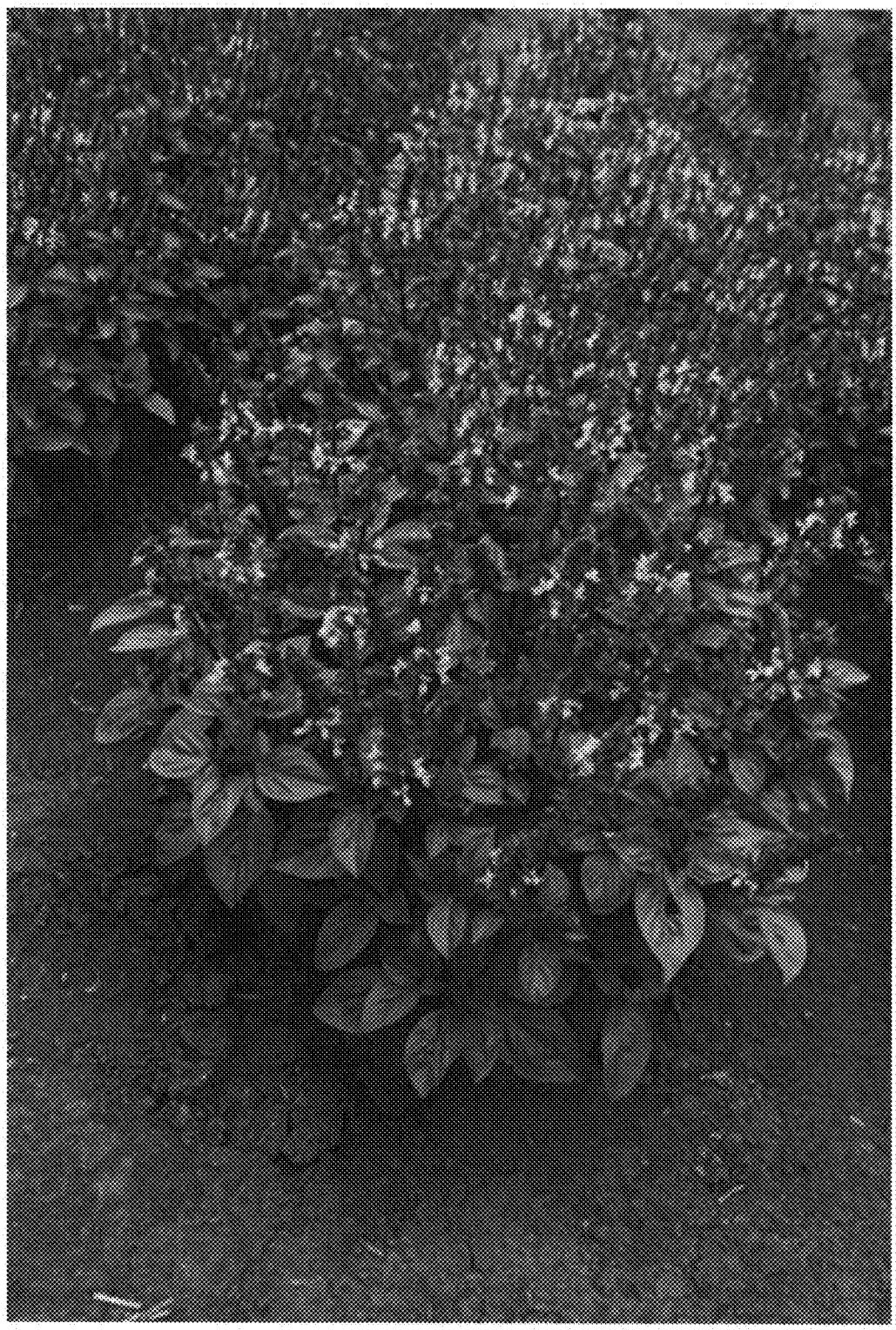
FIG. 3 is a photograph of multiple plants of the new variety.
Figure 4:
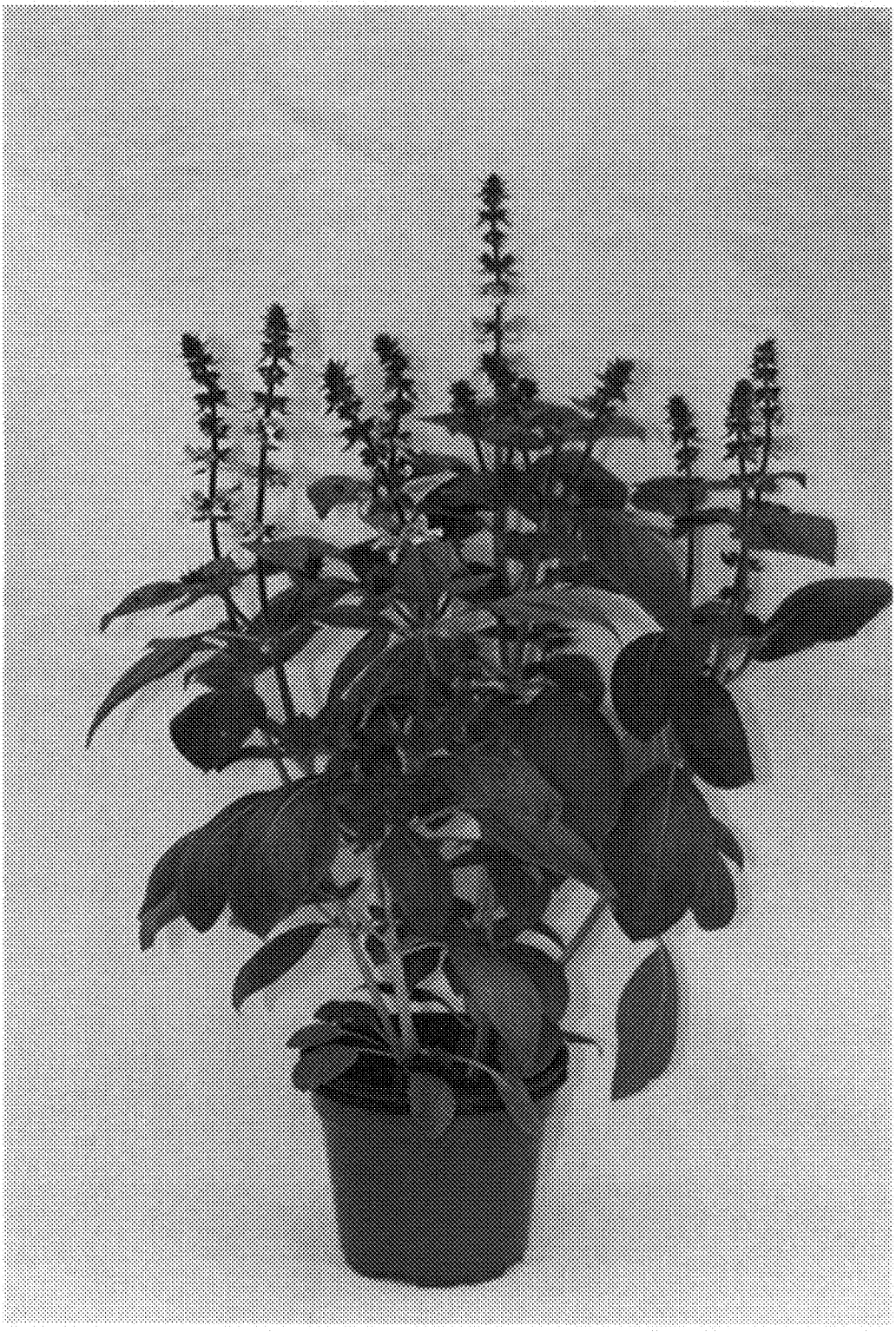
FIG. 4 is a photograph of a potted plant of the new variety.
Figure 5:
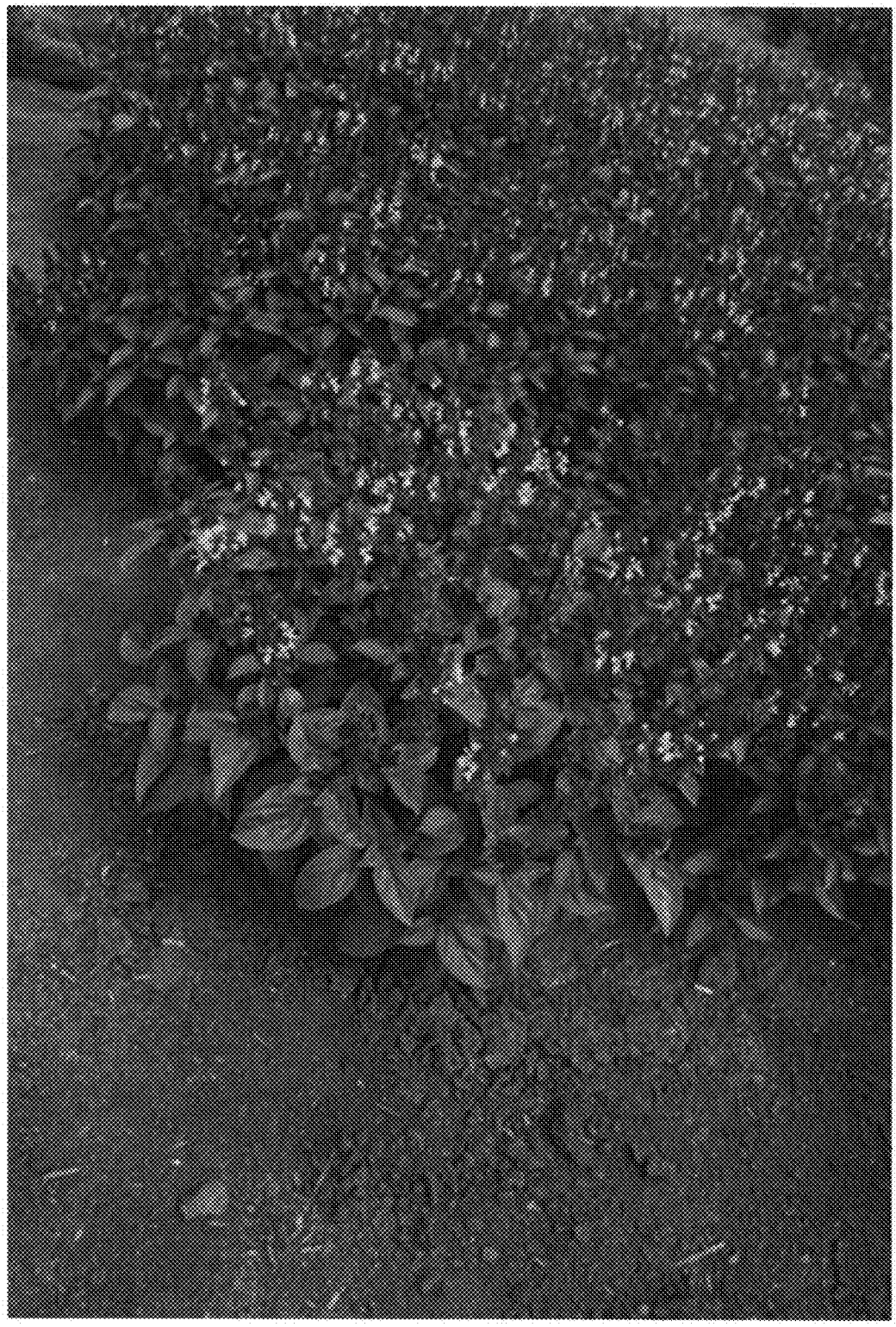
FIG. 5 is a photograph of a field of plants of the new variety.
Figure 6:
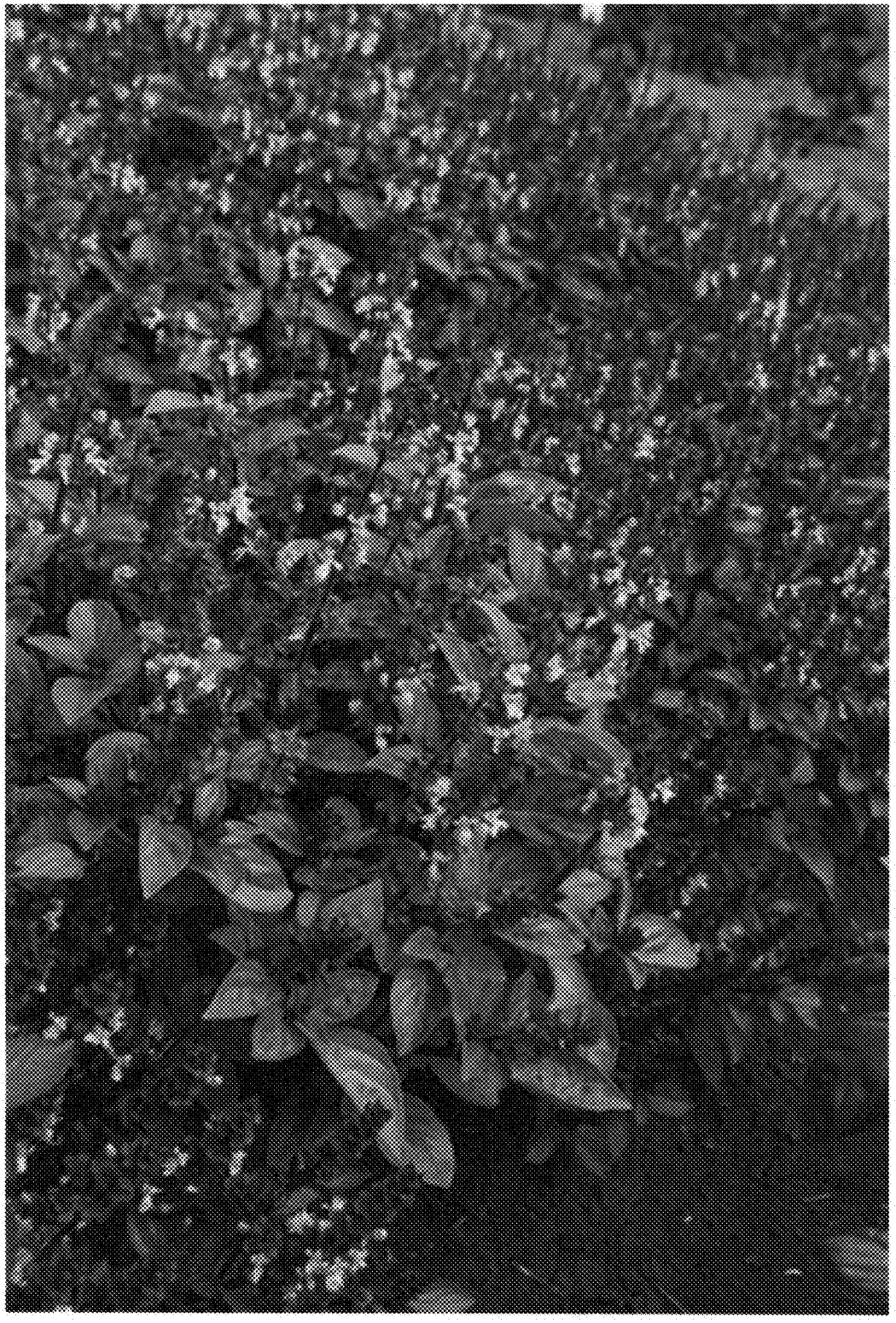
FIG. 6 is a another photograph of a field of plants of the new variety.
Figure 7:
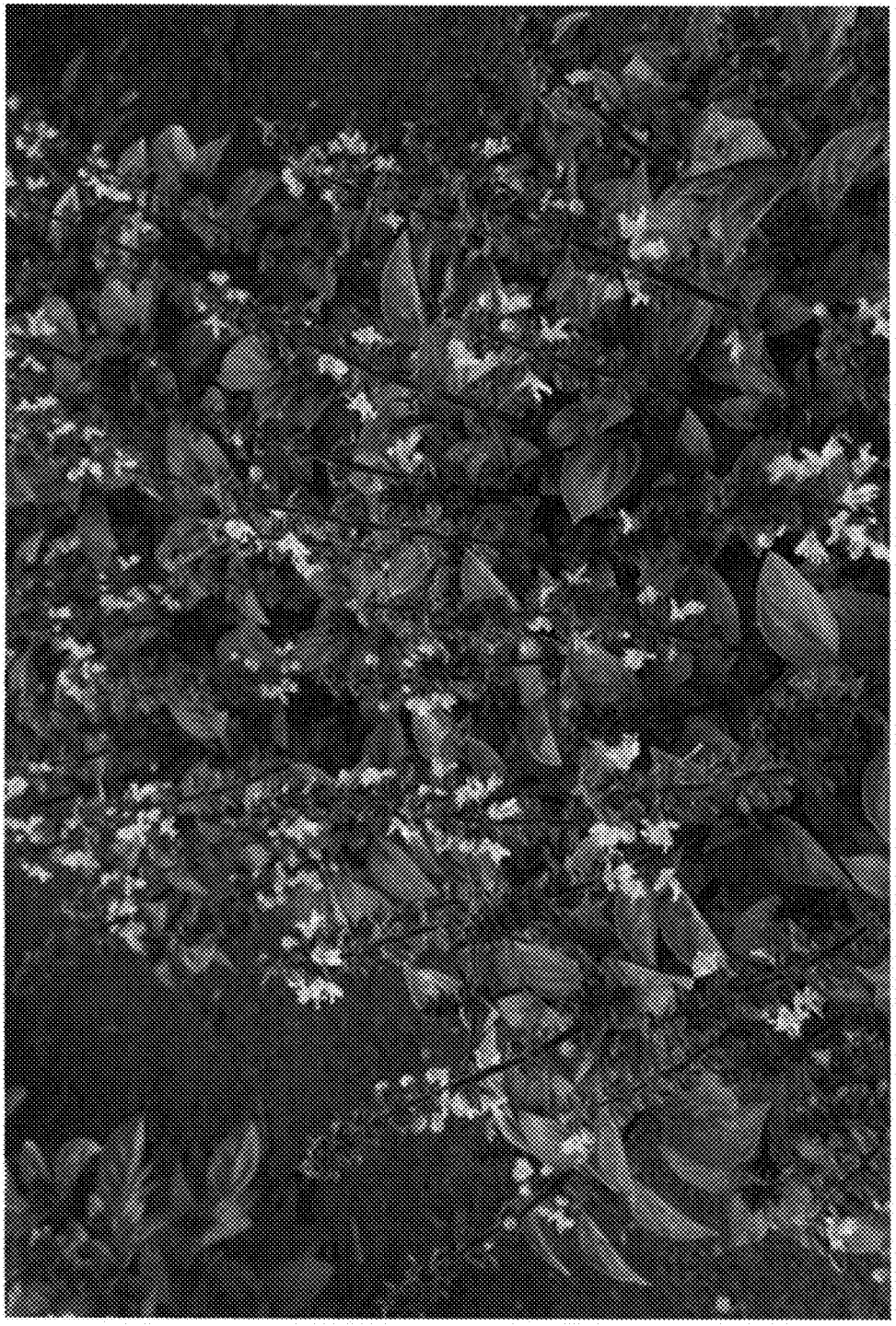
FIG. 7 is a close-up photograph of the flowers of the new variety.
Figure 8:
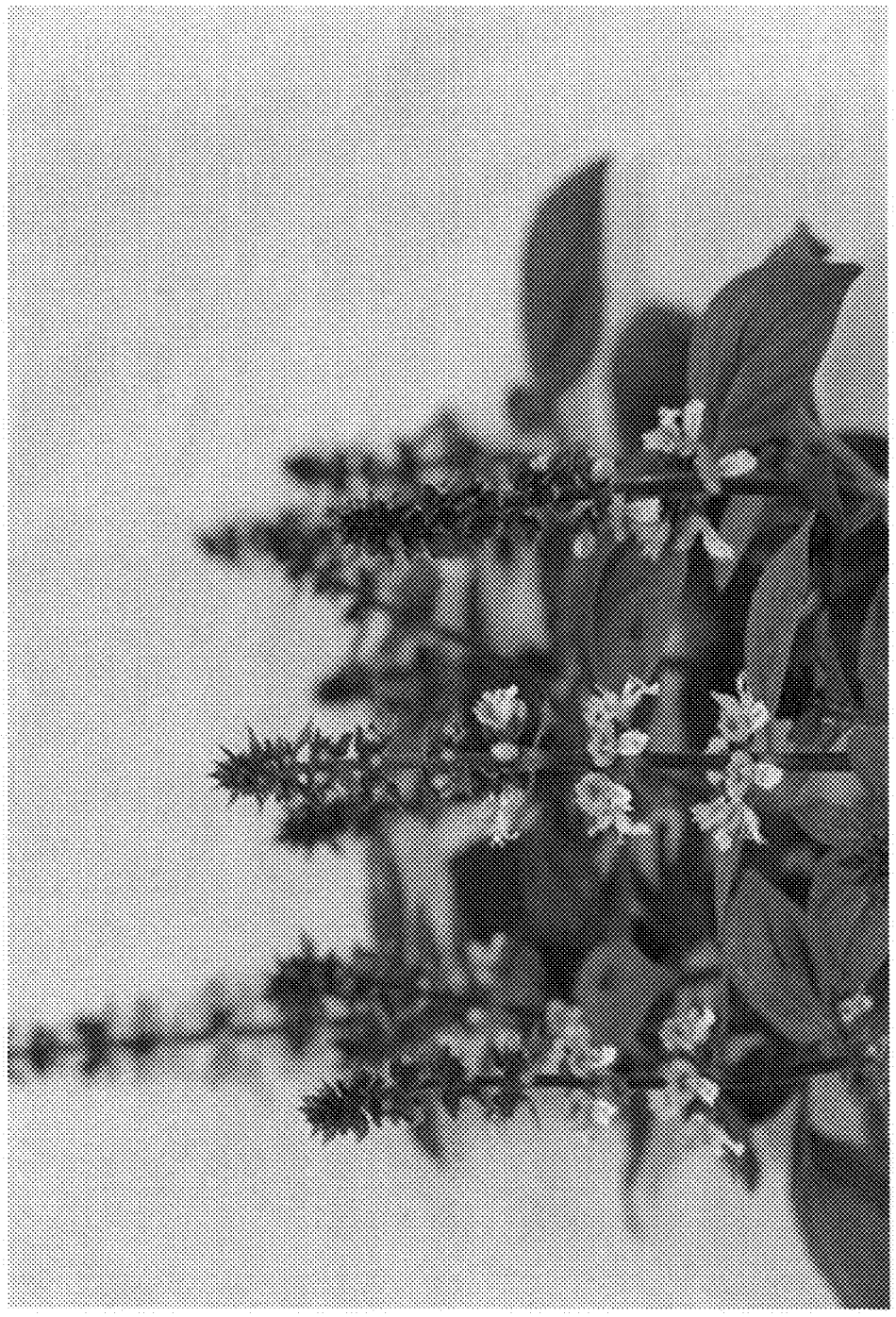
FIG. 8 is another close-up photograph of the flowers of the new variety.
Figure 9:
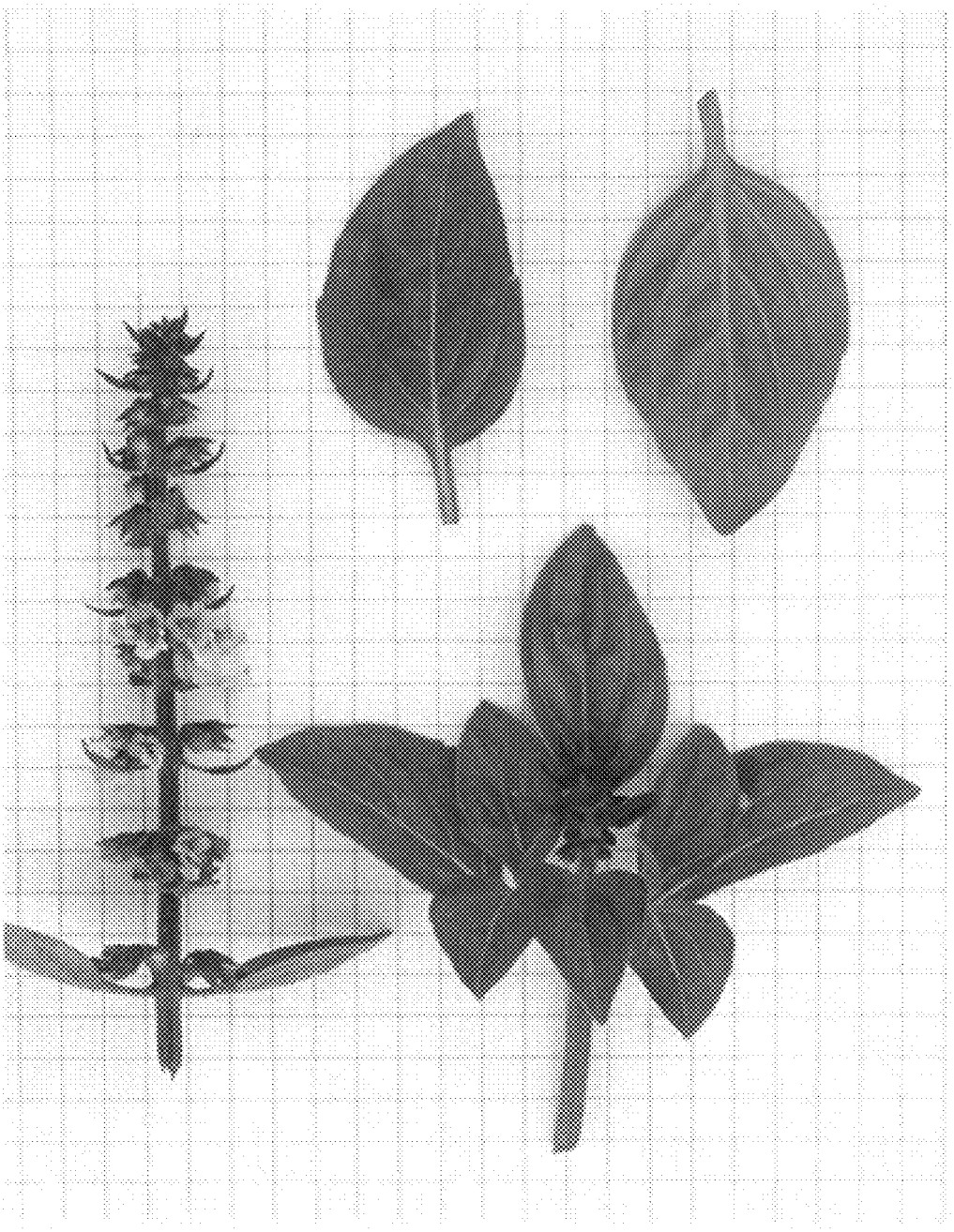
FIG. 9 is a photograph of detached leaves and flowers of the new variety.

Time to initiate roots: 5 days at 22° C.

Time to produce a rooted plant: 9 days at 22° C.

Root description: Finely branched white roots with a fibrous habit.

Form: Erect with a round habit.

Height from soil to top of plant: 55 cm.

Plant diameter: 40 cm.

Vigor: Conglobate, ovate, with a very high-branching habit.

Main stem:

*Length.*—55 cm.

*Width.*—0.7 cm.

*Color.*—At the base, the color starts as Yellow-Green Group RHS 145A and upwardly turns dark pink and violet to Violet Group RHS 83B at the top.

*Number of branches.*—15-25.

*Node spacing.*—2-3 cm.

Leaves:

*Arrangement.*—Decussate; pinnate.

*Number of leaves per plant.*—About 300.

*Length.*—4 cm.

*Width.*—3 cm.

*Shape of leaf (generally).*—Elliptic.

*Shape of apex.*—Acute.

*Shape of base.*—Elliptic.

*Texture.*—No pubescence is present.

*Aspect.*—Horizontal to downwards.

*Margin type.*—Medium serration present.

*Upper surface color.*—Green Group RHS 137C.

*Lower surface color.*—Green Group RHS 137C.

*Veins.*—Upper surface description and color: Pinnate; Green Group RHS 141D. Lower surface description and color: Pinnate; Yellow-Green Group RHS 145A.

*Petiole.*—Length: 0.5-1.5 cm. Diameter: 1-2 mm. Color: Yellow-Green Group RHS 145B. Texture: Hairy. Shape: Round.

Reproductive organs: 1 pistil and 4 stamens present.

Flowers:

*Natural flowering season.*—End of June through September in the Brandenburg Region of Germany.

*Number of flowers per plant.*—About 300.

*Fragrance.*—Aromatic.

*Longevity.*—6-8 weeks.

*Flower type.*—Labiate.

*Flower height.*—0.7 cm.

*Flower diameter.*—0.5 cm.

*Petal color.*—Upper surface: Purple Group RHS 75C and White Group RHS 999D. Lower surface: Purple Group RHS 75C and White Group RHS 999D.

Seed description: Sterile.

Disease/pest resistance: Tolerant to *Fusarium oxysporum* and *Botrytis cinerea.*

Weather tolerance: Very tolerant to rain and cold nights (down to 8° C.).

Harvesting season: Early summer to fall outdoors; year round indoors.

Flavor: Very spicy.

Aroma: Spicy.

Essential oils: Linalool-methylchavicol-type.

Productivity/yield per acre:

*Fresh.*—6 tons per acre.

*Dried.*—0.9 tons per acre.

Average life span: 5 months.

Use: Multiple uses. The new variety can be used as a pot plant, ornamental plant, culinary herb, or fresh and dried herb.

Fresh shelf life: Over 1 week under cool conditions (5-8° C.).

I claim:

1. A new and distinct variety of basil plant named 'Green Fortune' as herein described and illustrated.

* * * * *